(12) United States Patent
Strauss et al.

(10) Patent No.: US 10,191,127 B2
(45) Date of Patent: Jan. 29, 2019

(54) MAGNETIC RESONANCE IMAGING SYSTEM INCLUDING A PROTECTIVE COVER AND A CAMERA

(71) Applicant: Aspect Imaging Ltd., Shoham (IL)

(72) Inventors: Noa Strauss, Petah Tikva (IL); Irad Leiser, Ramat Gan (IL); Aviad Dezorayev, Holon (IL); Shmuel Azulay, Tel Aviv (IL); Uri Rapoport, Moshav Ben Shemen (IL)

(73) Assignee: Aspect Imaging Ltd., Shoham (IL)

( * ) Notice: Subject to any disclaimer, the term of this patent is extended or adjusted under 35 U.S.C. 154(b) by 0 days.

(21) Appl. No.: 15/402,437

(22) Filed: Jan. 10, 2017

(65) Prior Publication Data

US 2017/0146619 A1     May 25, 2017

Related U.S. Application Data

(63) Continuation-in-part of application No. 13/903,057, filed on May 28, 2013, now Pat. No. 9,562,956.
(Continued)

(51) Int. Cl.
    *G01R 33/422*     (2006.01)
    *A61B 5/055*     (2006.01)
(Continued)

(52) U.S. Cl.
    CPC .......... *G01R 33/283* (2013.01); *A61B 5/0035* (2013.01); *A61B 5/0077* (2013.01);
(Continued)

(58) Field of Classification Search
USPC .................. 324/300–322; 600/407–435; 382/128–131
See application file for complete search history.

(56) References Cited

U.S. PATENT DOCUMENTS 4,543,959 A    10/1985   Sepponen
4,613,820 A     9/1986   Edelstein
(Continued)

FOREIGN PATENT DOCUMENTS

CN     101185383     5/2008
CN     201846566     5/2011
(Continued)

OTHER PUBLICATIONS

Eberich et al., Functional MRI in neonates using neonatal head coil and MR compatible incubator, NeuroImage 20 (2003) 683-692.
(Continued)

*Primary Examiner* — Melissa Koval
*Assistant Examiner* — Tiffany Fetzner
(74) *Attorney, Agent, or Firm* — Pearl Cohen Zedek Latzer Baratz LLP

(57) ABSTRACT

A protective cover for an open bore MRI is disclosed. The cover comprises a semi-permeable barrier, MRI shielding, and physical shielding; is at least partially transparent; and it comprises fluid connection means for providing a fluid connection between an inner open bore of said open bore MRI and an environment external to said open bore MRI. A camera operable in a MRI system is disclosed. The camera can be positioned adjacent to an RF shield (e.g., the protective cover) and external to a bore of the MRI system. The camera can generate an image of at least a portion of a patient during operation of the MRI system.

12 Claims, 7 Drawing Sheets

Related U.S. Application Data

(60) Provisional application No. 61/720,440, filed on Oct. 31, 2012.

(51) Int. Cl.
   *G01R 33/28* (2006.01)
   *A61B 5/00* (2006.01)
   *H04N 5/225* (2006.01)

(52) U.S. Cl.
   CPC ............ *A61B 5/055* (2013.01); *G01R 33/288* (2013.01); *G01R 33/422* (2013.01); *H04N 5/2253* (2013.01); *H04N 5/2257* (2013.01)

(56) References Cited

U.S. PATENT DOCUMENTS

| | | |
|---|---|---|
| 4,651,099 A | 3/1987 | Vinegar |
| 4,875,485 A | 10/1989 | Matsutani |
| 4,968,961 A | 11/1990 | Miyajima et al. |
| 5,153,546 A | 10/1992 | Laskaris |
| 5,346,022 A | 9/1994 | Krivec |
| 5,436,607 A | 7/1995 | Chari et al. |
| 5,565,831 A | 10/1996 | Dorri et al. |
| 5,883,558 A | 3/1999 | Laskaris et al. |
| 6,128,522 A | 10/2000 | Acker et al. |
| 6,157,278 A | 12/2000 | Katznelson et al. |
| 6,208,142 B1 | 3/2001 | Wagshul |
| 6,278,274 B1 | 8/2001 | Biglieri et al. |
| 6,323,647 B1 | 11/2001 | Anderson et al. |
| 6,502,042 B1 | 12/2002 | Eid et al. |
| 6,611,702 B2 | 8/2003 | Rohling et al. |
| 7,071,692 B2 | 7/2006 | Branch |
| 7,274,192 B2 | 9/2007 | Havens |
| 7,378,848 B2 | 5/2008 | Gao et al. |
| 7,399,220 B2 * | 7/2008 | Kriesel ................. A01K 11/008 452/157 |
| 7,486,982 B2 | 2/2009 | Branch |
| 7,614,692 B2 | 11/2009 | Biaud |
| 7,621,815 B2 | 11/2009 | Bosserdet, Jr. |
| 7,760,084 B2 | 7/2010 | Jensen et al. |
| 7,777,491 B2 | 8/2010 | Gao et al. |
| 8,087,203 B2 | 1/2012 | Boesel et al. |
| 8,118,488 B2 | 2/2012 | Gregerson |
| 8,375,295 B2 | 2/2013 | Zalewski et al. |
| 8,525,116 B2 * | 9/2013 | Schulz ................. G01T 1/1603 250/363.02 |
| 8,555,578 B2 | 10/2013 | Hushek |
| 8,583,294 B2 | 11/2013 | Villano et al. |
| 8,807,084 B2 | 8/2014 | Rapoport et al. |
| 8,851,018 B2 | 10/2014 | Rapoport et al. |
| 8,896,310 B2 | 11/2014 | Rapoport et al. |
| 8,924,848 B2 | 12/2014 | Klinger |
| 8,924,869 B2 | 12/2014 | Fellman |
| 8,930,831 B2 | 1/2015 | Bartomeli et al. |
| 8,984,426 B2 | 3/2015 | Endoh et al. |
| 9,003,318 B2 | 4/2015 | Magnusson et al. |
| 9,055,912 B2 | 6/2015 | Graumann et al. |
| 9,599,683 B2 * | 3/2017 | Armstrong ........... G01R 33/283 |
| 2001/0038489 A1 | 11/2001 | Nakamura et al. |
| 2002/0123681 A1 | 9/2002 | Zuk et al. |
| 2002/0173717 A1 | 11/2002 | Rohling et al. |
| 2003/0016518 A1 | 1/2003 | Arz |
| 2003/0088175 A1 | 5/2003 | Branch |
| 2004/0106844 A1 | 6/2004 | Lonneker-Lammers |
| 2004/0116799 A1 | 6/2004 | Srinivasan |
| 2004/0127786 A1 | 7/2004 | Schmit et al. |
| 2004/0135687 A1 | 7/2004 | Keene |
| 2004/0147833 A1 | 7/2004 | Czipott et al. |
| 2004/0194989 A1 | 10/2004 | Branch |
| 2004/0196043 A1 | 10/2004 | Branch |
| 2005/0027189 A1 | 2/2005 | Branch |
| 2005/0242817 A1 | 11/2005 | Hoult |
| 2006/0022670 A1 | 2/2006 | Kumar et al. |
| 2006/0084857 A1 | 4/2006 | Massengill et al. |
| 2006/0267585 A1 | 11/2006 | Havens |
| 2007/0135704 A1 | 6/2007 | Branch |
| 2007/0203481 A1 | 8/2007 | Gregg et al. |
| 2007/0232894 A1 | 10/2007 | Feenan |
| 2007/0238950 A1 | 10/2007 | Vija et al. |
| 2008/0021317 A1 | 1/2008 | Sumanaweera |
| 2008/0103388 A1 | 5/2008 | Maschke et al. |
| 2008/0122441 A1 | 5/2008 | Hayakawa |
| 2008/0171931 A1 | 6/2008 | Maschke |
| 2008/0204028 A1 | 8/2008 | DeVries et al. |
| 2008/0234571 A1 | 9/2008 | Hay et al. |
| 2008/0281187 A1 | 11/2008 | Massengill et al. |
| 2009/0209846 A1 * | 8/2009 | Bammer ................ A61B 5/055 600/421 |
| 2009/0213997 A1 | 8/2009 | Maschke |
| 2010/0066368 A1 | 3/2010 | Gao et al. |
| 2010/0145358 A1 | 6/2010 | Maschke |
| 2010/0154325 A1 | 6/2010 | Boesel et al. |
| 2010/0219347 A1 * | 9/2010 | Schulz ................. G01T 1/1603 250/363.04 |
| 2010/0245543 A1 * | 9/2010 | Greer ................... G01R 33/283 348/46 |
| 2011/0162652 A1 | 7/2011 | Rapoport |
| 2011/0186049 A1 | 8/2011 | Rapoport |
| 2011/0234347 A1 | 9/2011 | Rapoport |
| 2011/0274238 A1 | 11/2011 | Maschke |
| 2011/0280364 A1 | 11/2011 | Maschke |
| 2011/0280380 A1 | 11/2011 | Maschke |
| 2011/0282184 A1 | 11/2011 | Klingenbeck et al. |
| 2011/0304333 A1 | 12/2011 | Rapoport |
| 2012/0071745 A1 | 3/2012 | Rapoport |
| 2012/0073511 A1 | 3/2012 | Rapoport |
| 2012/0077707 A1 | 3/2012 | Rapoport |
| 2012/0119742 A1 | 5/2012 | Rapoport |
| 2013/0079624 A1 | 3/2013 | Rapoport |
| 2013/0109956 A1 | 5/2013 | Rapoport |
| 2013/0150656 A1 | 6/2013 | Falk et al. |
| 2013/0237803 A1 | 9/2013 | Rapoport |
| 2013/0328559 A1 | 12/2013 | Rapoport |
| 2013/0328560 A1 | 12/2013 | Rapoport |
| 2013/0328563 A1 | 12/2013 | Rapoport |
| 2014/0050827 A1 | 2/2014 | Rapoport |
| 2014/0051973 A1 | 2/2014 | Rapoport |
| 2014/0051974 A1 | 2/2014 | Rapoport |
| 2014/0051976 A1 | 2/2014 | Rapoport |
| 2014/0099010 A1 | 4/2014 | Rapoport |
| 2014/0103927 A1 | 4/2014 | Rapoport |
| 2014/0117989 A1 | 5/2014 | Rapoport |
| 2014/0128725 A1 | 5/2014 | Rapoport |
| 2014/0139216 A1 | 5/2014 | Rapoport |
| 2014/0142914 A1 | 5/2014 | Rapoport |
| 2014/0152302 A1 | 6/2014 | Rapoport |
| 2014/0152310 A1 | 6/2014 | Rapoport |
| 2014/0158062 A1 | 6/2014 | Rapoport |
| 2014/0230850 A1 | 8/2014 | Rapoport |
| 2014/0257081 A1 | 9/2014 | Rapoport |
| 2014/0266203 A1 | 9/2014 | Rapoport |
| 2014/0300358 A1 | 10/2014 | Rapoport |
| 2014/0354282 A1 * | 12/2014 | Kusik .................. G01R 33/283 324/322 |
| 2014/0378821 A1 | 12/2014 | Rapoport |
| 2014/0378825 A1 | 12/2014 | Rapoport |
| 2015/0005618 A1 | 1/2015 | Dumoulin |
| 2015/0059157 A1 | 3/2015 | Rapoport |
| 2015/0059655 A1 | 3/2015 | Rapoport |
| 2015/0065788 A1 | 3/2015 | Rapoport |
| 2015/0077105 A1 | 3/2015 | Rapoport et al. |
| 2015/0137812 A1 | 5/2015 | Rapoport |
| 2015/0141799 A1 | 5/2015 | Rapoport |
| 2015/0226817 A1 | 8/2015 | Pourrahimi |
| 2015/0230766 A1 | 8/2015 | Wang et al. |
| 2016/0089054 A1 | 3/2016 | Rapoport |
| 2017/0143271 A1 * | 5/2017 | Gustafsson .......... G01R 33/283 |

(56) References Cited

U.S. PATENT DOCUMENTS

| | | | |
|---|---|---|---|
| 2017/0146619 A1* | 5/2017 | Strauss | G01R 33/283 |
| 2017/0181912 A1 | 6/2017 | Rapoport et al. | |

FOREIGN PATENT DOCUMENTS

| | | |
|---|---|---|
| DE | 102008009673 | 8/2009 |
| DE | 102008009674 | 8/2009 |
| DE | 102011109375 | 2/2013 |
| DE | 202013104656 | 10/2013 |
| EP | 0187691 | 7/1986 |
| EP | 2607977 | 6/2013 |
| IL | 226488 | 5/2013 |
| JP | S5961763 | 9/1984 |
| JP | 04317630 | 11/1992 |
| JP | 2007-252741 | 10/2007 |
| WO | WO1998048756 | 11/1998 |
| WO | WO2004029644 | 4/2004 |
| WO | WO2012004797 | 1/2012 |
| WO | WO2013115847 | 8/2013 |

OTHER PUBLICATIONS

International Standard, CEI IEC 60601-1-8, Second Edition, Oct. 2006, Medical electrical equipment, Part 1-8:1-166.

SASO IEC 60601-1-10, Medical electrical equipment, Part 1-10: General requirements for basic safety and essential performance, Collateral Standard: Requirements for the development of physiologic closed-loop controllers, 2008, 1-36.

International Standard, CEI IEC 60601-1, Third Edition, Dec. 2005, Medical electrical equipment, Part 1, 1-393.

International Standard, CEI IEC 60601-2-19, Edition 2.0, Feb. 2009, Medical electrical equipment—Part 2-19: Particular requirements for the basic safety and essential performance of infant incubators, 1-80.

\* cited by examiner

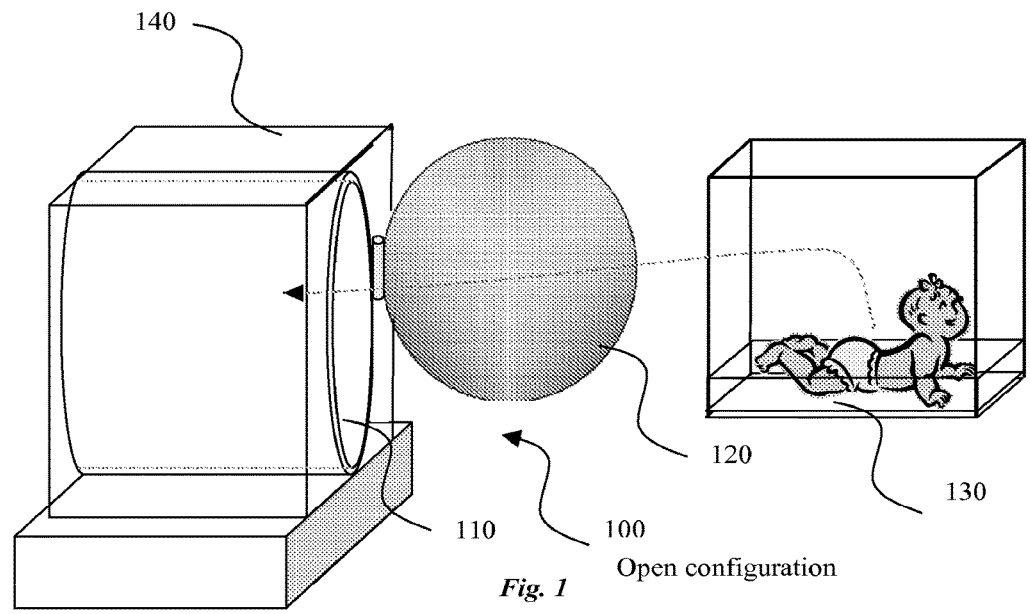
140, 110, 120, 130, 100
*Fig. 1* Open configuration
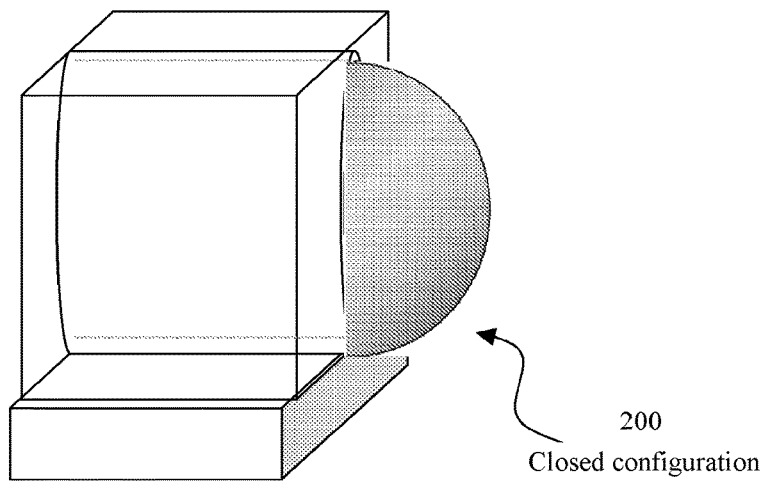
200
Closed configuration
*Fig. 2*

300
Close configuration

600
CLOSED configuration,

Polygonal  Curved  Flat  Having an incubator
a   b   c   d

Hinge   Telescopic

MAGNETIC RESONANCE IMAGING SYSTEM INCLUDING A PROTECTIVE COVER AND A CAMERA

CROSS REFERENCE TO RELATED APPLICATIONS

This application is a continuation-in-part of U.S. patent application Ser. No. 13/903,057, filed on May 28, 2013, which claims priority to U.S. Provisional Application No. 61/720,440, filed on Oct. 31, 2012, all of which are incorporated herein by reference in their entirety.

FIELD OF THE INVENTION

The present invention generally relates to the field of magnetic resonance imaging systems (MRI), and more particularly, to a shielding cover of an MRI opening and to generating a camera image of a patient during procedure of an MRI system.

BACKGROUND OF THE INVENTION

The use of magnetic resonance imaging (MRI) as a diagnostic tool is a fairly recent innovation in the medical field.

In MRI scanning, the MRI apparatus system operates as a large magnet wherein the protons align with the strong magnetic field but are easily disturbed by a brief radio frequency pulse of very low energy so as to alter their alignment. As the protons return to their orientation with the magnetic field, they release energy of a radio frequency that is strongly influenced by the biochemical environment. The released energy is detected and mathematically analyzed for display as a two dimensional proton density image according to the signal intensity from each tissue.

The potential dangers associated with MRI scanners include a strong magnetic field within the apparatus and surrounding area. The magnetic force may convert loose metal objects into unguided missiles directed at the MRI apparatus, which involves iron, steel and other metal objects striking personnel within the vicinity of an MRI apparatus. These objects have been unwittingly introduced into the magnetic field of the MRI. It is well known in the art that MRI devices are usually located within a shielded room for improved results and also to lessen the impact of the device on surrounding operations. However, the problem persists of metal objects being negligently introduced into the magnetic field by personnel entering the room or the extended magnetic field of the MRI apparatus.

It therefore remains a long felt and unmet need to provide an MRI apparatus system having an MRI shield that is configured for MRI devices in order to prevent the introduction of loose metal objects into the strong uniform main static magnetic field of an MRI apparatus.

It therefore remains a long felt and unmet need to provide an apparatus having an MRI shield for MRI devices to prevent the introduction of objects into the magnetic field of an MRI apparatus.

During MRI imaging of patients, it can be difficult to know a state of a patient while the patient is within the MRI being imaged. For example, for a patient that is having difficulty breathing but not on life support, it can be desirable to know whether the patient is breathing or not. In another example, for a baby undergoing an MRI, it can be desirable for the parents to view the baby while the baby is in an MRI.

Therefore, it can be desirable to monitor the state of a patient while undergoing an MRI.

SUMMARY OF THE INVENTION

There is provided in accordance with a preferred embodiment of the present invention a protective cover for an open bore MRI, the cover characterized in that:

(a) it comprises a semi-permeable barrier, MRI shielding, and physical shielding, (b) it is at least partially transparent; and, (c) it comprises fluid connection means for providing a fluid connection between an inner open bore of the open bore MRI and an environment external to the open bore MRI.

There is further provided in accordance with a preferred embodiment of the present invention the cover as defined above, wherein the semi-permeable barrier is made at least partially of connected strands of flexible or ductile material.

There is further provided in accordance with a preferred embodiment of the present invention the cover as defined above, wherein the flexible or ductile material comprises a material selected from the group consisting of metal and fiber.

There is further provided in accordance with a preferred embodiment of the present invention the cover as defined above, wherein the semi-permeable barrier is constructed of material selected from the group consisting of copper, paramagnetic materials, ferromagnetic materials, and any combination thereof.

There is further provided in accordance with a preferred embodiment of the present invention the cover as defined above, wherein the semi-permeable barrier has a structure of a mesh, a web or a net.

There is further provided in accordance with a preferred embodiment of the present invention the cover as defined above, wherein the cover is transparent.

There is further provided in accordance with a preferred embodiment of the present invention the cover as defined above, wherein the MRI shielding is an RF shielding type.

There is further provided in accordance with a preferred embodiment of the present invention the cover as defined above, wherein the cover is configured such that when the cover is in place, an opening of the open bore MRI is completely covered by the cover.

There is further provided in accordance with a preferred embodiment of the present invention the cover as defined above, wherein the cover comprises attaching means matching corresponding attaching means on the open bore MRI, thereby functioning as a door for opening and closing the open bore MRI.

There is further provided in accordance with a preferred embodiment of the present invention the cover as defined above, wherein the attaching means are configured such that upon opening, the cover remains attached to the open bore MRI.

There is further provided in accordance with a preferred embodiment of the present invention the cover as defined above, wherein the cover has a shape selected from the group consisting of: tubular, cone shaped, cup shaped, cylindrical, sleeve like, and hollow with a perimeter configured to match an bore of the open bore MRI and an internal shape configured to match an object placed within.

There is further provided in accordance with a preferred embodiment of the present invention the cover as defined above, wherein the cover has a shape which can be mated to an incubator within the open bore MRI.

There is further provided in accordance with a preferred embodiment of the present invention the cover as defined above, wherein the cover further comprises a ring frame disposed about the perimeter of the cover.

There is further provided in accordance with a preferred embodiment of the present invention the cover as defined above, wherein the magnetic shielding extends over an area at least equal to an open area of the open bore.

There is further provided in accordance with a preferred embodiment of the present invention the cover as defined above, wherein the cover is rotatable.

One aspect of the present invention provides magnetic resonance imaging (MRI) system including: a MRI device having a bore to accommodate at least a portion of a patient, the bore having an aperture; a radiofrequency (RF) shield to cover the aperture and to prevent an external RF radiation from entering the bore and an RF radiation emitted by the MRI device from exiting the bore; and a camera positioned adjacent to the RF shield and external to the bore, the camera to generate an image of at least a portion of the patient during operation of the MRI device.

In some embodiments, the RF shield includes a mesh, a net or any combination thereof.

In some embodiments, the RF shield further includes a plurality of holes, each hole of the plurality of holes having a longitudinal dimension and a transverse dimension, and wherein a ratio of the longitudinal dimension to the transverse dimension of each of the plurality of holes is at least 5:1.

In some embodiments, a shape of the holes is at least one of: a square, a rectangular, an oval or any combination thereof.

In some embodiments, a focal length of the camera is based on a distance of at least a portion of the patient from the RF shield such that a clear image of the at least portion of the patient is generated by the camera.

In some embodiments, a focal length of the camera is substantially greater than a distance between the camera and the RF shield.

In some embodiments, the MRI device has an enclosure to at least partly envelope the bore, and wherein the camera is positioned within the enclosure.

Another aspect of the present invention provides a method of generating a camera image of at least a portion of a patient positioned in a magnetic resonance imaging (MRI) system, the method includes: preventing radiofrequency (RF) radiation generated by the MRI system from exiting a measurement volume of the MRI system; and obtaining a camera image of at least a portion of the patient positioned within the MRI, the at least one camera image having a desired clarity.

In some embodiments, the method further includes transmitting a light into the measurement volume to illuminate the at least portion of the patient.

In some embodiments, the camera image is a photo, a video, or any combination thereof.

In some embodiments, the method further includes adjusting a focal length of a camera obtaining the camera image based on a position of the at least portion of the patient relative to the camera.

In some embodiments, the method further includes preventing the RF radiation from impinging upon the camera.

One advantage of the invention can include allowing a state of a patient to be monitored during MRI imaging. Another advantage of the invention is that a baby having an MRI can be viewed by the parents, thus providing comfort and assurance that the baby is doing well while being imaged. Another advantage of the invention can include allowing healthcare professionals to monitor baby lips color as an indicator to normal blood oxygen level thus, for example, eliminating a need to stop the MRI imaging. Another advantage of the invention is that it can allow healthcare professionals to indicate a problem of ejecting an intubation tube at intubated baby without a need to stop the MRI imaging. Another advantage of the invention can include allowing healthcare professionals to visualize a patient while having an MRI, such that, for example, critically ill patients can be attended to if their health state changes during the MRI.

BRIEF DESCRIPTION OF THE DRAWINGS

In order to understand the invention and to see how it may be implemented in practice, a few preferred embodiments will now be described, by way of non-limiting example only, with reference to be accompanying drawings, in which:

FIG. 1 illustrates a protective cover of an open bore MRI in its open configuration in accordance with a preferred embodiment of the present invention;

FIG. 2 illustrates a protective cover of an open bore MRI in its close configuration when no imaging occurs, in accordance with a preferred embodiment of the present invention;

DETAILED DESCRIPTION OF THE INVENTION

Figure 3:
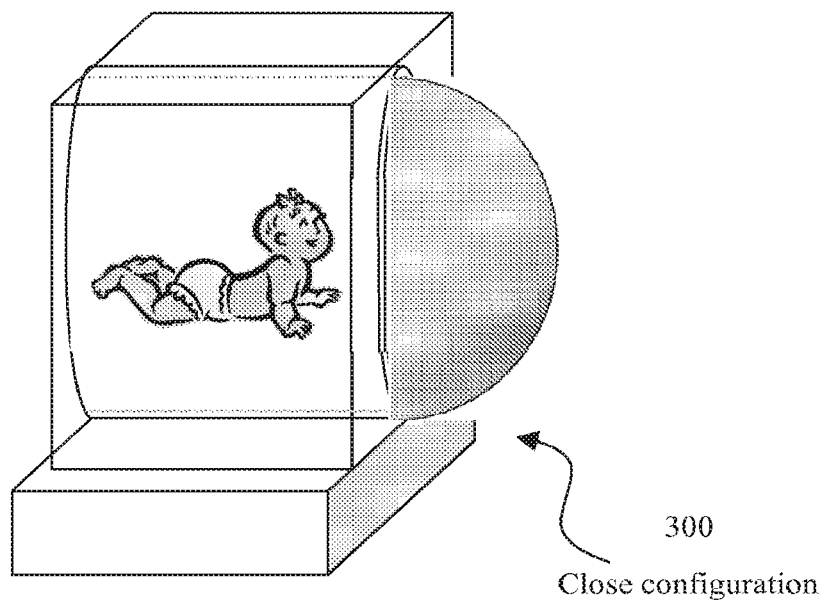
FIG. 3 illustrates a protective cover of an open bore MRI in its close configuration in an imaging procedure, in accordance with a preferred embodiment of the present invention.

The following description is provided so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide an apparatus for covering MRI opening.

The term 'magnetic resonance device' (MRD), 'magnetic resonance imaging (MRI,) or 'magnetic resonance system', specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) or any combination thereof. The term, in this invention, also applies to any other analyzing and imaging instruments comprising a volume of interest, such as computerized tomography (CT), ultrasound (US) etc. The MRD hereby disclosed is optionally a portable MRI device, such as the ASPECT-MR Ltd commercially available devices, or a commercially available non-portable device. Moreover, the term 'MRD' interchangeably refers in general to any non-incubator medical devices, at least temporary accommodating the neonate.

As used herein, the term 'incubator' may include isolate-like devices which are self-contained incubator units that provides a controlled heat, humidity, and oxygen microenvironment for the isolation and care of premature and low-birth weight neonates. The apparatus is often made of a clear plastic material and has a large door and portholes for easy access to the infant with a minimum of heat and oxygen loss. A servo control mechanism constantly monitors the infant's temperature and controls the heat within the unit. The incubator may further be mounted on a movable cart or the like.

As used herein, the term "open bore" is related to the opening of an MRI (magnetic resonance imaging) system having designed diameter to accommodate a patient, in which the patient is inserted in order to lie within a large cylindrical magnet.

FIG. 1 presents an illustration of a protective cover 120 for an open bore 110 of a MRI 140. The cover characterized in that: (a) it comprises a semi-permeable barrier, MRI shielding, and physical shielding, (b) it is at least partially transparent; and, (c) it comprises fluid connection means for providing a fluid connection between an inner open bore of the open bore MRI and an environment external to the open bore MRI.

Reference is now made to FIG. 1 which presents an open configuration 100 of the cover. The cover may be opened vertically or horizontally to an upper position or a lower position of the open bore MRI.

The cover is located upon the front opening of the MRI. The cover may comprise attaching means matching corresponding attaching means on the open bore MRI, thereby functioning as a door for opening and closing the open bore MRI. Furthermore the attaching means are configured such that upon opening, the cover remains attached to the open bore MRI.

The cover may further be hingably mounted, to at least on one side thereof, to a portion of the open bore MRI, corresponding to one side of the opening by a hinge mechanism. The cover may further be extracted from the MRI open bore.

In another embodiment of the present invention, the cover is configured such that when the cover is in place, an opening of the open bore MRI is completely covered by the cover and further protects from undesirable magnetic field leakage.

The cover has a shape selected from the group consisting of: tubular, cone shaped, cup shaped, cylindrical, sleeve like, and hollow with a perimeter configured to match an bore of the open bore MRI and an internal shape configured to match an object placed within.

In another embodiment of the present invention, a handle (not shown) may further be provided at the outer side portion of the cover. In accordance with this structure, the cover is hingably movable when the user pulls the handle to open the opening or pushes the handle to close the MRI opening. The cover may further be rotatable.

In another embodiment of the present invention, the cover may be partially made of a transparent material or transparent texture which may function as a window door. The window door may be made of a transparent glass material to provide highest-visibility RF view window of a subject. The cover may be partially made of glass whilst imbedded with copper. Furthermore, the cover may be fully made of a glass platform. Since the glass provides a full sealing and provides a constant temperature a ventilation system may be further adapted.

In another embodiment of the present invention, the cover may be partially made of semi-permeable barrier which is made of connected strands of metal, fiber, or other flexible or ductile material. The semi-permeable barrier has a structure of a mesh, a web or net which has many attached or woven strands. The semi-permeable barrier is further selected from the group consisting of: copper, paramagnetic materials which have a relative magnetic permeability greater or equal to unity attracted to magnetic fields, ferromagnetic materials or combination thereof. In order to create a strong magnetic shield the cover may be formed partially from paramagnetic materials. Paramagnetic materials exhibit, at least over an appreciable temperature range, magnetic susceptibilities that adhere to the Curie or Curie-Weiss laws. Furthermore, the paramagnet material have the advantage that they do not retain any magnetization in the absence of an externally applied magnetic field, resulting from thermal motion randomizes the spin orientations. The cover may be formed partially from ferromagnetic metal or their alloys, such as Co, Fe, $Fe_2O_3$, $FeOFe_2O_3$, $NiOFe_2O_3$, $CuOFe_2O_3$, $MgOFe_2O_3$, MnBi, MnSb, Ni, $MnOFe_2O_3$, $Y_3Fe_5O_{12}$, $CrO_2$, MnAs, Gd, Dy, or EuO. The cover may further be of a combination of copper, ferromagnetic metals and paramagnetic metals or the like.

In another embodiment of the present invention, the cover is characterized by a magnetic shielding to protect the environment from the MRI magnetic field. The magnetic shielding is an RF shielding which can be made of virtually types of metals. The most prominent types used for MRI shielding are copper, galvanized steel, and aluminum. Other metals are not typically used due to drawbacks such as ease of handling or modifications, and corrosion.

The copper RF shield may be a copper sheeting wrapped around and bolted together to form a cover. This type of shielding is lightweight, easily modified to address field or site discrepancies, and provides a lasting RF enclosure. Another type of RF shield system may be a pan-form shield constructed entirely of metal. This system is bolted together to form the cover. This system can utilize galvanized steel, stainless steel, or aluminum, depending upon the preference of the MRI system manufacturer. The cover further provides a magnetic field shield and may further prevent a projectile effect of ferromagnetic objects.

The cover seals the open bore 110 of the MRI device 140 in a manner of a Faraday shield adequately. The cover mesh overlap significantly and is in contact with the MRI open bore.

Reference is now made to FIGS. 2 and 3 which present a close configuration of the protective cover of an open bore MRI. FIG. 2 presents a close configuration when no imaging procedure is performed 200 on the other hand, FIG. 3 present a close configuration when an imaging procedure is occurred 300. The cover can be closed in a vertical direction or horizontal direction to an upper position or a lower position of the open bore MRI.

In another embodiment of the present invention, the cover may further comprises a ring frame disposed about the perimeter of the cover. The frame may have a structure of an annular rim for surrounding the cover and further providing better sealing in a latch manner to maintain the cover fully opened or closed. The cover is coupled to the MRI in a manner which prevents exiting of a magnetic field from the imaging system. Therefore the magnetic shielding extends over an area at least equal to an open area of the open bore.

Figure 4:
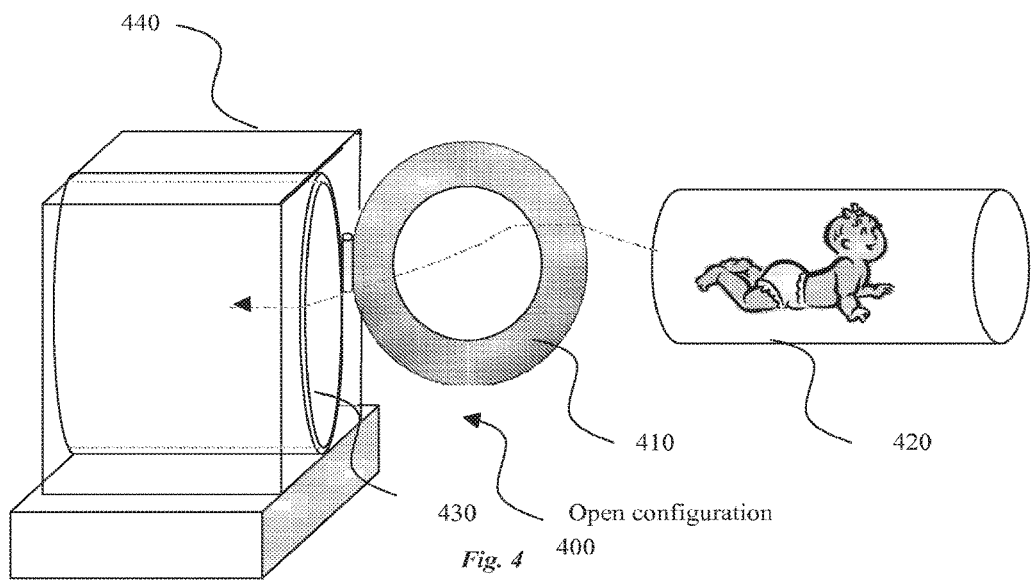
FIG. 4 illustrates a protective cover of an open bore MRI comprising an incubator in its open configuration, in accordance with a preferred embodiment of the present invention.

Reference is now made to FIG. 4 which presents a protective cover 410 of an open bore 430 of a MRI 440 comprising an incubator with a subject 420 such a child, baby or infant, in its open configuration 400. The cover has a shape which can be mated to an incubator within the open bore MRI. The cover is characterized in that: (a) it comprises a semi-permeable barrier, MRI shielding, and physical shielding, (b) it is at least partially transparent; and (c) it comprises fluid connection means for providing a fluid connection between an inner open bore of the open bore MRI and an environment external to the open bore MRI.

The cover is located in the front of the MRI opening. The cover may further be hingably mounted, to at least one side thereof, to a portion of the MRI opening tunnel, corresponding to one side of the opening by a hinge configuration.

Figure 5:
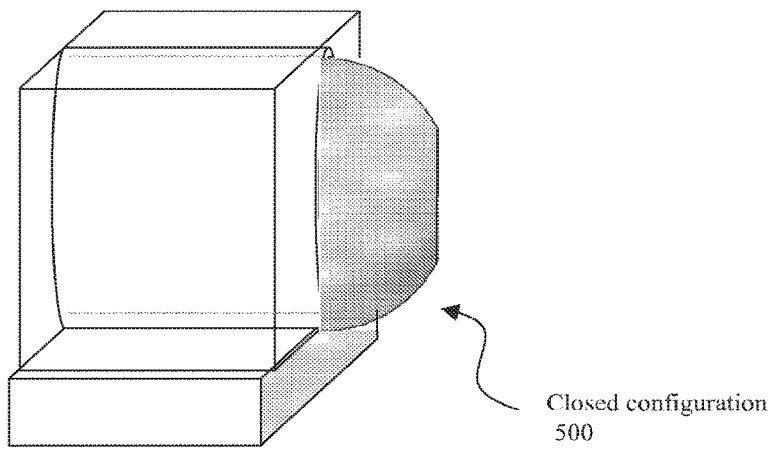
FIG. 5 illustrates protective cover of an open bore MRI comprising an incubator in its close configuration when no imaging occurs, in accordance with a preferred embodiment of the present invention.

Reference is now made to FIG. 5 which presents a protective cover of an open bore MRI in its close configuration 500, not including an incubator with a subject.

Figure 6:
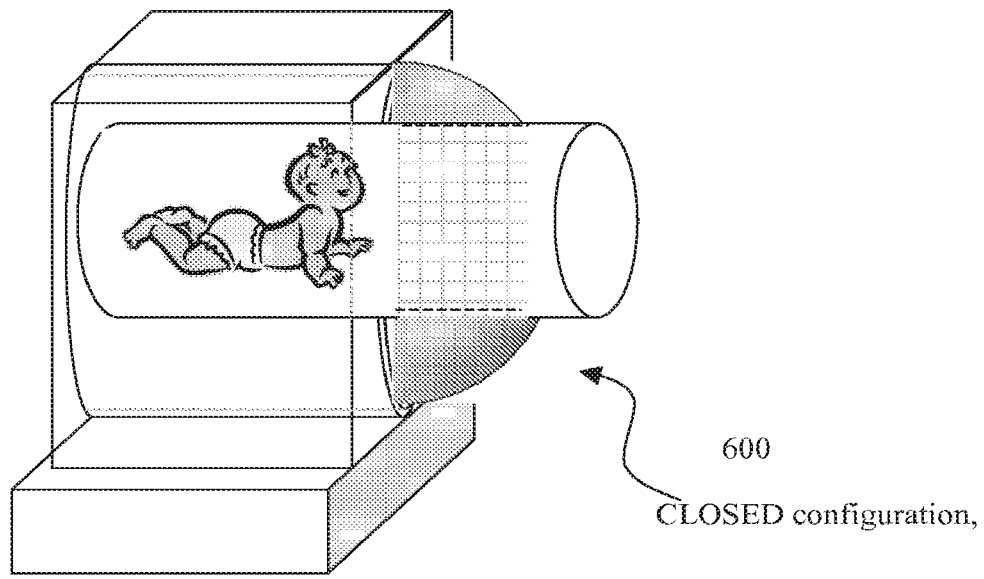
FIG. 6 illustrates a protective cover of an open bore MRI comprising an incubator in its close configuration in an imaging procedure, in accordance with a preferred embodiment of the present invention; and, FIG. 7 illustrates protective cover structures and positions, in accordance with a preferred embodiment of the present invention.

Reference is now made to FIG. 6 which presents a protective cover of an open bore MRI in its close configuration 600 whilst comprising an incubator with a subject such as a child, a baby or an infant.

The cover has a shape selected from the group consisting of: tubular, cone shaped, cup shaped, cylindrical, sleeve like, and hollow with a perimeter configured to match an bore of the open bore MRI and an internal shape configured to match an object placed within. The cover may further have a structure protruding from the MRI open bore in order to cover and shield the exterior portion of an incubator. The cover may further be applied upon the incubator in a wearable manner. The cover edge may further have a planner structure as illustrated in FIGS. 5 and 6.

Figure 7:
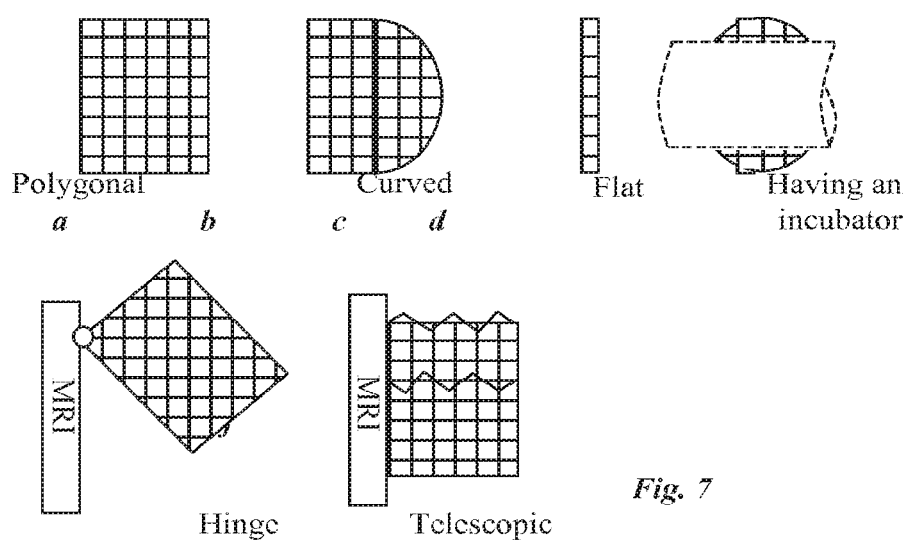

Reference is now made to FIG. 7 which illustrates a variety of structures which the cover may have and be positioned. The cover may have a curved structure (a), a polygonal structure (b), or a flat structure (c). Furthermore the cover may have a structure protruding from the exterior of the MRI open bore in order to contain the protruding portion of the incubator (d).

The cover may further be hingably mounted (e), to at least one side thereof, to a portion of the MRI opening tunnel, corresponding to one side of the opening by a hinge mechanism. The cover may further be extracted from the MRI open bore. The cover may further positioned in a telescopic structure (f).

Figure 8:
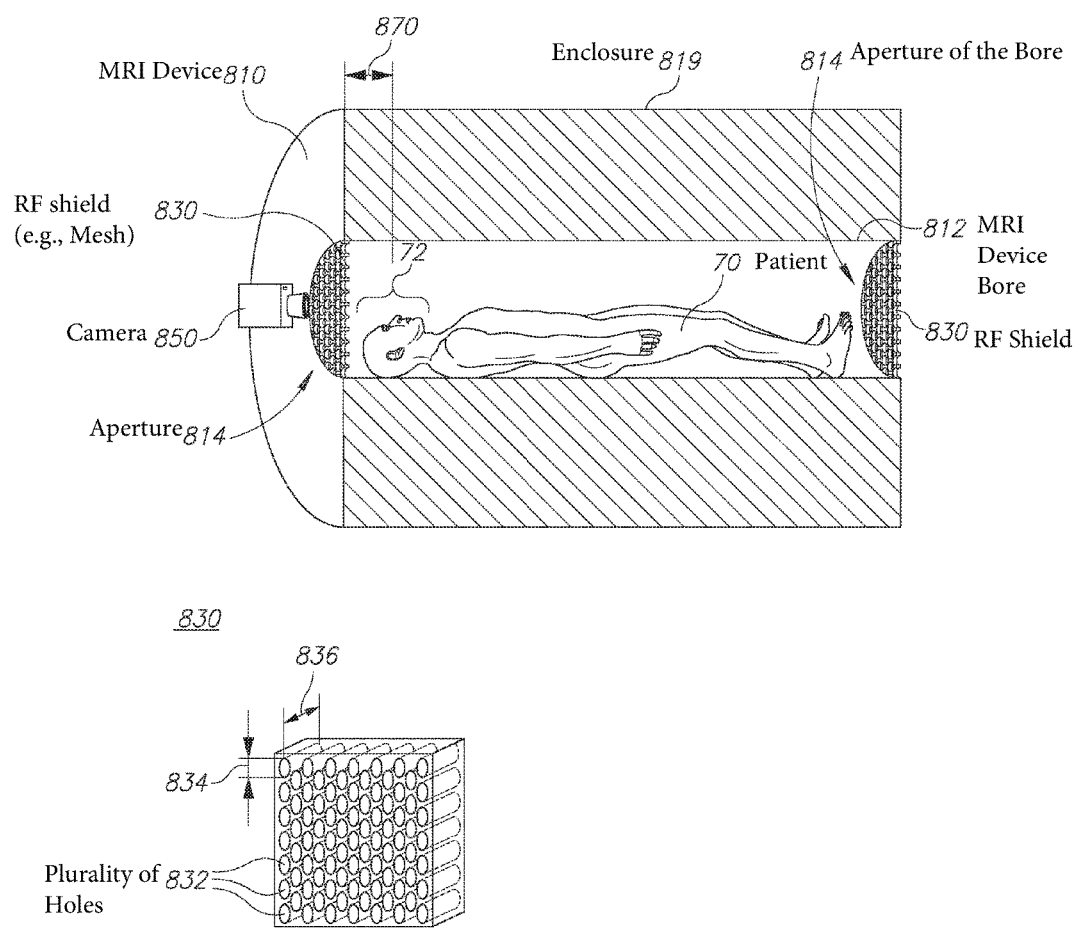
FIG. 8 is an illustration of a camera in a magnetic resonance imaging (MRI) system, according to some embodiments of the invention.

FIG. 8 is an illustration of a camera 850 in a magnetic resonance imaging (MRI) system, according to some embodiments of the invention.

The MRI system can include a MRI device 810. The MRI device 810 can include a bore 812 to accommodate a patient 70 and/or at least a portion of the patient 70. The bore 812 can include at least one aperture 814.

The MRI system can include at least one radiofrequency (RF) shield 830. The RF shield(s) 830 can cover the aperture(s) 814 of the bore 112 and/or can prevent an external RF radiation from entering the bore 812 and an RF radiation emitted by the MRI device 810 from exiting the bore 812.

The RF shield 830 can include a plurality of holes 832 (e.g., as shown in FIG. 8), where each of the holes 832 can have a length 836 and a diameter 834. In some embodiments, a ratio of the length 836 to the diameter 834 of each hole 832 is at least 5:1. The holes 832 are circle shaped. In various embodiments, the holes 832 are square, rectangular, oval, or any shape. In these various shaped embodiments, each hole can have a ratio of length to width of at least 5:1. In some embodiments, the RF shield 830 is the cover 120, 410, as described above. In some embodiments, the RF shield 830 is a mesh, a net and/or any combination thereof (e.g., as described above).

The MRI system can include a camera 850 positioned adjacent to the RF shield 830 and external to the bore 812 (e.g., as shown in FIG. 8). The camera 850 can generate an image of at least a portion 72 of the patient 70 during operation of the MRI device 810. The camera 850 can be positioned at a predetermined distance 870 from the portion 72 of the patient 70 and/or from the RF shield 830.

The camera 850 can have a focal length value $f_1$. The focal length value $f_1$ can be predetermined based on the distance 870 between the camera 850 and/or the RF shield 830 to the portion 72 of the patient 70 such that a clear image of the at least portion of the patient can be generated by the camera. In some embodiments, the distance 870 is substantially greater than the focal length value $f_1$. In some embodiments, the focal length value $f_1$ is substantially greater than a distance between the camera 850 and the RF shield 830 (e.g., the camera can be adjacent to the RF shield, as shown in FIG. 8). Accordingly, the RF shield 830 is not in focus of the camera 850 and/or is evenly smeared on the image generated by the camera. Accordingly, the RF shield 830 does not obscure the image generated by the camera. As a result a clear image of the patient 70 and/or the portion 72 can be generated by the camera 850.

Figure 9A:
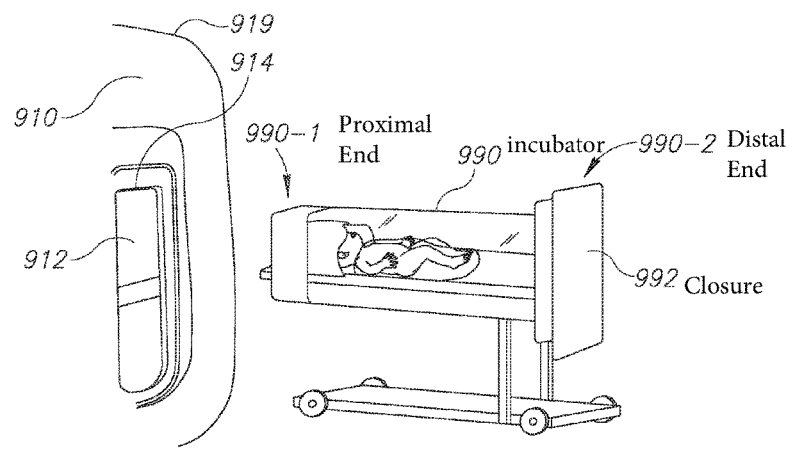
FIG. 9A is an illustration of an neonate MRI system, according to some embodiments of the invention.
Figure 9B:
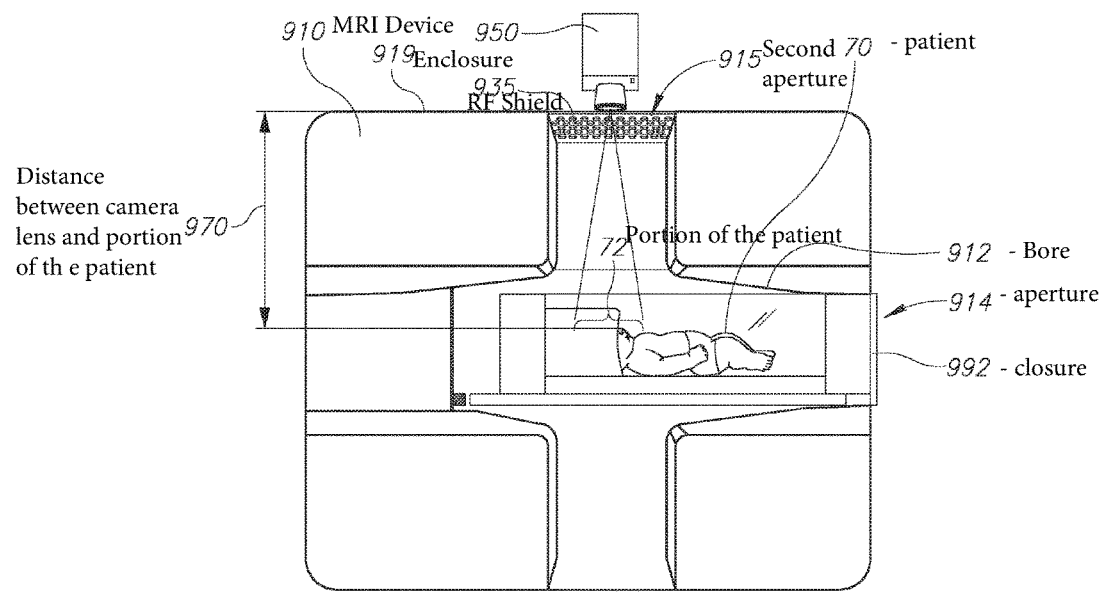
FIG. 9B is an illustration of a camera in a neonatal magnetic resonance imaging (MRI) system, according to some embodiments of the invention.

FIG. 9A is an illustration of a neonate MRI system, according to some embodiments of the invention. FIG. 9B is an illustration of a camera 950 in a neonatal magnetic resonance imaging (MRI) system, according to some embodiments of the invention.

The neonatal MRI system can include an MRI device 910 that can receive an incubator 990. The incubator 990 can accommodate a patient 70 (e.g., a neonate as shown in FIGS. 9A-9B) and/or can have a proximal end 990-1 and/or a distal end 990-2. The incubator 990 can be inserted into a bore 912 of the MRI device 910 from the proximal end 990-1. The incubator 990 has a closure 992 at the distal end 990-2. The closure 992 can shut an aperture 914 of the bore 912 upon an insertion of the incubator 990. The closure 992 can include an RF shield 930 (not shown), for example, embedded within the closure 992, to prevent an external RF radiation from entering the bore 912 and an RF radiation emitted by the MRI device 910 from exiting the bore 912. In some embodiments, the RF shield 930 is the cover 120, 410 and/or RF shield 830 (e.g., as described above) and/or has predetermined dimensions to be embedded within the closure 992.

The MRI device 910 can include a second aperture 915 (e.g., as shown in FIG. 9B). The second aperture 915 can be covered by an RF shield 935. In some embodiments, the RF shield 935 is the cover 120, 410 and/or RF shield 830 (e.g., as described above) and/or has predetermined dimensions to cover the aperture 914. In some embodiments, the RF shield 935 is a mesh, a net and/or any combination thereof. The neonatal MRI system can include a camera 950 that can be positioned adjacent to the RF shield 935 covering the second aperture 915, external to the bore 912 and/or at a predetermined distance 970 from the portion 72 of the patient 70 (e.g., as shown in FIG. 9B). The second aperture 915 can have predetermined dimensions to allow the desired portion 72 of the patient 70 to be imaged by the camera 950. For example, the second aperture 915 can be directly above the desired portion 72 of the patient 70 to be imaged by the camera 950, such that there can be a direct line of sight between the camera 950 and the desired portion 72 of the patient 70. In some embodiments, the second aperture 915 can be positioned such that the line of sight between the camera 950 and the desired portion 72 of the patient 70 is at an angle. As is apparent to one of ordinary skill in the art, the second aperture 915 can be positioned at any location within the MRI system that can allow the camera to capture a desired portion 72 of the patient 70 and the camera 950 to be shielded by the RF shield 935.

The camera 950 can have a focal length value $f_2$. The focal length value $f_2$ can be predetermined based on the distance 970 between the camera 950 and/or the RF cover 935 to the portion 72 of the patient 70 such that a clear image of the at least portion of the patient can be generated by the camera. In some embodiments, the distance 970 is substantially greater than the focal length value $f_2$. For example, the focal length value $f_2$ can range between 25-45 mm and/or the distance 970 can range between 350-550 mm. In some embodiments, the focal length value $f_2$ is substantially greater than a distance between the camera 950 and the RF shield 935 (e.g., the camera can be adjacent to the RF shield, as shown in FIG. 9B). Accordingly, the RF shield 935 is not in focus of the camera 950 and/or is evenly smeared on the image generated by the camera. Accordingly, the RF shield 935 does not obscure the image generated by the camera and/or a clear image of the patient 70 and/or the portion 72 can be generated by the camera 950.

The cameras 850, 950 can be positioned external to an enclosures 819, 919 enveloping at least a portion of the bore 812, 919 and/or the MRI device 810, 910, respectively (e.g., as shown in FIG. 8, FIG. 9B). In some embodiments, the cameras 850, 950 are positioned within the enclosure 819 and/or the enclosure 919.

In some embodiments, the cameras 850, 950 can take still images. In some embodiments, the cameras 850, 950 can capture a video. In some embodiments, the cameras 850, 950 can transmits still and/or video images via wired or wireless communication (e.g., Wifi, Bluetooth, and/or other wireless communications as are known in the art). In some embodiments, the camera is a camera WAT-233T being manufactured by Watec.

One advantage of the present invention can include obtaining camera images of a patient while the patient is within an MRI device while simultaneously providing RF shielding to the camera. Another advantage of the invention can include that a baby having an MRI can be viewed by the parents, thus providing comfort and assurance that the baby is doing well while being imaged. The RF shield (e.g., the RF shields 830, 935) can prevent an external RF radiation (e.g., generated by the cameras 850, 950) from entering the bore (e.g., the bores 812, 912) and/or affect operation of the MRI device (e.g., the MRI devices 810, 910). The RF shields can also prevent from an RF radiation emitted by the MRI device from exiting the bore and/or affect, for example, operation of the cameras.

Another advantage of the present invention can include obtaining camera images of a patient while the patient is within an MRI device, of the MRI apparatus system, in which the obtained camera images are of a desirable clarity wherein the presence of the RF shielding does not hinder the clinical usability of the obtained camera image. The camera (e.g., cameras 850, 950) can have the focal length value being substantially smaller than the distance between the portion of the patient (e.g., the distances 870, 970) being examined by the MRI apparatus system and/or the focal length value can be a focal length that allows the camera to be positioned immediately adjacent to the RF shield (e.g., RF shield 830, 935), such that the RF shield does not obscure the obtained camera image that is generated by the camera, because the location and positioning of the RF shield in the inventive MRI apparatus system only reduces a portion of an illumination present in the obtained camera image that was generated by the utilization of the camera.

Figure 10:
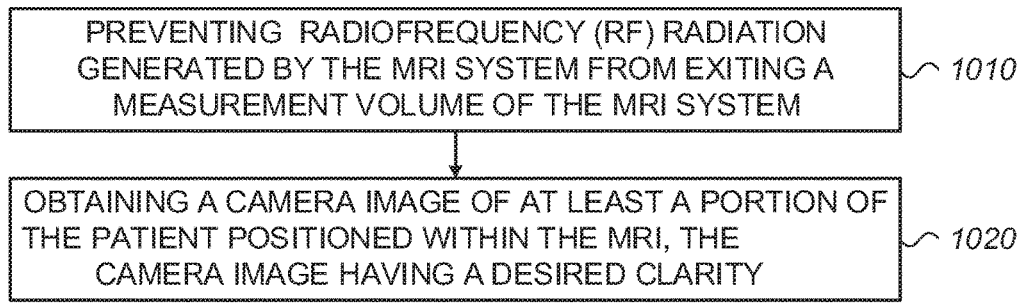
FIG. 10 is a flowchart illustrating a method of generating a camera image of at least a portion of a patient positioned in a magnetic resonance imaging (MRI) system, according to some embodiments of the invention.

FIG. 10 is a flowchart illustrating a method of generating an obtained camera image of at least a portion of a patient (e.g., patient 70, as described above in FIG. 8) positioned in a magnetic resonance imaging (MRI) system (e.g., MRI system as described above in FIG. 8 and FIGS. 9A-9B), according to some embodiments of the invention.

The method can include preventing at step 1010 radiofrequency (RF) radiation generated by the MRI system from exiting a measurement volume (e.g., bore 812, as described above in FIG. 8 and/or bore 912, as described in FIGS. 9A-9B) of the MRI system.

The method can include obtaining at step 1020 a camera image of at least a portion of the patient positioned within the MRI, the obtained at least one camera image having a desirable clarity wherein the presence of the RF shielding does not hinder the clinical usability of the obtained camera image.

In some embodiments, the method can further include transmitting a light into the measurement volume to illuminate the at least portion of the patient. In some embodiments, the camera image can be a photo, a video, or any combination thereof. In some embodiments, the method can further include adjusting a focal length of a camera obtaining the camera image based on a position of the at least portion of the patient relative to the camera. In some embodiments, the method can further include preventing the RF radiation from impinging upon the camera.

The invention claimed is:

1. A magnetic resonance imaging (MRI) system comprising:
  a MRI device having a bore that accommodates at least a portion of a patient, the bore also having an aperture;
  a protective, semi-permeable, and at least partially transparent cover, located at the aperture of the bore, that contains RF shielding preventing an external RF radiation from entering the bore;
  wherein the protective, semi-permeable, and at least partially transparent cover when open allows the patient entry access into the bore of the MRI device and when closed provides a radiofrequency (RF) shield that covers the aperture of the bore while also preventing an RF radiation emitted by the MRI device from exiting the bore; and
  a camera positioned adjacent to the RF shielding of the protective semi-permeable, and at least partially transparent cover, where the camera is without electromagnetic shielding and the camera is positioned external to the bore and external to an area of RF radiation emitted within the bore, whereby the camera is still in proximity to a strong main static magnetic field produced by a large main magnetic field source that is part of the magnetic resonance imaging system itself, with the camera also being utilized in order to generate an image of at least the portion of the patient during operation of the MRI device where the presence of the RF shielding of the protective, semi-permeable, and at least partially transparent cover does not hinder the clinical usability of the generated image.

2. The MRI system of claim 1, wherein the RF shield of the protective, semi-permeable, and at least partially transparent cover, comprises:
   a mesh,
   a net or
   a combination thereof.

3. The MRI system of claim 1, wherein the RF shield of the protective, semi-permeable, and at least partially transparent cover, further comprises a plurality of holes, each role of the plurality of holes having a longitudinal dimension and a transverse dimension, and wherein a ratio of the longitudinal dimension to the transverse dimension of each of the plurality of holes is at least 5:1.

4. The MRI system of claim 3, wherein a shape of the holes is at least one of:
   a square,
   a rectangle,
   an oval or
   a combination thereof.

5. The MRI system of claim 1, wherein a focal length of the camera is based on a distance of at least the portion of the patient from the RF shield of the protective, semi-permeable, and at least partially transparent cover such that the presence of the RF shield does not prevent a diagnostically usable image of at least the portion of the patient from being generated by the camera.

6. The MRI system of claim 1, wherein a focal length of the camera is substantially greater than a distance that is located between the camera and the RF shield of the protective, semi-permeable, and at least partially transparent cover.

7. The MRI system of claim 1, wherein the MRI has an enclosure to at least partly envelope the bore, and wherein the camera is positioned external to the enclosure.

8. A method of generating a camera image of at least a portion of a patient positioned in a magnetic resonance imaging (MRI) system, the method comprising:

preventing radiofrequency (RF) radiation generated by the MRI system from exiting and RF radiation generated outside of the MRI system from entering a measurement volume of the MRI system via a protective, semi-permeable, and at least partially transparent RF shielding cover, located at an aperture of a bore of the MRI system, that has both an open and a closed state, and when the protective, semi-permeable, and at least partially transparent RF shielding cover is closed, the RF shielding then covers the aperture into the bore and the measurement volume of the MRI system;

generating and obtaining a camera image of at least the portion of the patient positioned within the MRI system via a camera that is without electromagnetic shielding and positioned in a location external to an area of the generated RF radiation within the measurement volume, whereby the location of the positioned camera is still in proximity to a large magnet that produces a strong uniform main static magnetic field that is part of the magnetic resonance imaging system itself, and wherein the location of the positioned camera is also immediately adjacent to the RF shielding, of the protective, semi-permeable, and at least partially transparent RF shielding cover; and wherein the presence of the RF shielding does not hinder the clinical usability of the obtained camera image.

9. The method of claim 8, further comprising the camera transmitting a light into the measurement volume in order to illuminate at least the portion of the patient.

10. The method of claim 8, wherein the camera image is:
   a photo image,
   a video of images or
   a combination thereof.

11. The method of claim 8, further comprising adjusting a focal length of the camera in order to obtain the camera image based on a pre-established position of at least the portion of the patient relative to the camera.

12. The method of claim 8, further comprising preventing the RF radiation from impinging upon the camera, by the utilization of the immediately adjacent RF shielding of the protective, semi-permeable, and at least partially transparent cover.

* * * * *